United States Patent [19]

Ichinose et al.

[11] Patent Number: 5,702,691

[45] Date of Patent: Dec. 30, 1997

[54] FLAVANONOL DERIVATIVES AND HAIR-NOURISHING, HAIR GROWING COMPOSITIONS CONTAINING THE DERIVATIVES

[75] Inventors: Susumu Ichinose, Ishibashi-machi; Yoshinori Nishizawa, Utsunomiya; Atsushi Ohuchi, Ichikai-machi; Hideshi Kidena, Chiba; Mitsuyuki Hotta, Ujiie-machi, all of Japan

[73] Assignee: Kao Corporation, Tokyo, Japan

[21] Appl. No.: 682,568

[22] PCT Filed: Nov. 29, 1995

[86] PCT No.: PCT/JP95/02433

§ 371 Date: Sep. 16, 1996

§ 102(e) Date: Sep. 16, 1996

[87] PCT Pub. No.: WO96/16956

PCT Pub. Date: Jun. 6, 1996

[30] Foreign Application Priority Data

Dec. 2, 1994 [JP] Japan ................................. 6-299222
Dec. 2, 1994 [JP] Japan ................................. 6-299223

[51] Int. Cl.$^6$ ............................. A61K 7/06; C07D 311/32
[52] U.S. Cl. ........................ 424/70.1; 424/195; 424/405; 549/400; 514/456
[58] Field of Search ........................ 549/400; 424/70.1; 514/456

[56] References Cited

U.S. PATENT DOCUMENTS 3,689,663  9/1972  Kramer et al. ........................ 549/400

OTHER PUBLICATIONS

Journal of the Chemical Society, Section C: Organic Chemistry, vol. 17, pp. 2848–2855, 1971, W. P. Cullen et al., "The Algar–Flynn–Oyamada Oxidation of α-Substituted Chalcones α".

Tetrahedron Letters, No. 11, pp. 1023–1027, 1967, D.M.X. Donnelly, et al., "Oxidation of α-Methylchalcones".

Primary Examiner—Jose' G. Dees
Assistant Examiner—Laura L. Stockton
Attorney, Agent, or Firm—Oblon, Spivak, McClelland, Maier & Neustadt, P.C.

[57] ABSTRACT

The present invention relates to flavanonol derivatives represented by formula (1):

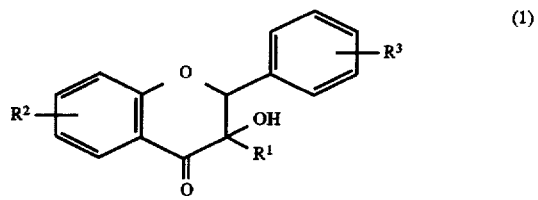

(wherein $R^1$ represents an alkyl group, and each of $R^2$ and $R^3$ represents a hydrogen atom, an alkyl group which may have a substituent, an alkoxyl group which may have a substituent, a hydroxyl group, a cyano group, or a halogen atom), as well as to hair-nourishing and hair-growing compositions containing the derivatives. The compounds accelerate differentiation and proliferation of hair matrix cells, thereby exhibiting remarkable hair-nourishing and hair-growing effects.

13 Claims, No Drawings

FLAVANONOL DERIVATIVES AND HAIR-NOURISHING, HAIR GROWING COMPOSITIONS CONTAINING THE DERIVATIVES

This application is a 371 of PCT/JP95/02433 filed Nov. 29, 1995.

TECHNICAL FIELD

The present invention relates to flavanonol derivatives and to hair-nourishing and hair-growing compositions containing the derivatives.

BACKGROUND ART

Hitherto, synthetic chemicals and natural extracts performing a variety of actions have been used as pharmaceuticals or medicated cosmetics which are intended to be used for hair nourishing and hair growing. Neither of these chemicals nor extracts exhibits sufficient effects if used in small amounts. Particularly, natural extracts have drawbacks that they give uncomfortable stimulation to portions of application if they are used in large amounts; that inflammation of the skin may be caused when they are used continuously; and that they may not be used in large amounts due to their color and odor.

Moreover, these conventional hair-nourishing and hair-growing agents do not directly act on differentiation and proliferation of hair matrix cells but exhibit their effects through normalizing the conditions of the scalp. Even in cases where they act on hair matrix cells, they do not exhibit satisfactory nourishing and growing effects on human hair.

Accordingly, it is still desired to develop hair-nourishing and hair-growing agents which exhibit remarkable hair-nourishing and hair-growing effects as well as hair loss-preventing effects through acting directly on differentiation and proliferation of hair matrix cells, and which are quite safe when used over long periods.

DISCLOSURE OF THE INVENTION

In view of the foregoing, the present inventors conducted careful studies, and as a result, they found that flavanonol derivatives represented by formula (1) described below act directly on differentiation and proliferation of hair matrix cells to exhibit remarkable hair-nourishing and hair-growing effects, and maintain high levels of safety over long periods of use. The present invention was accomplished based on these findings.

Accordingly, the present invention provides a hair-nourishing and hair-growing agent comprising a flavanonol derivative represented by the following formula (1):

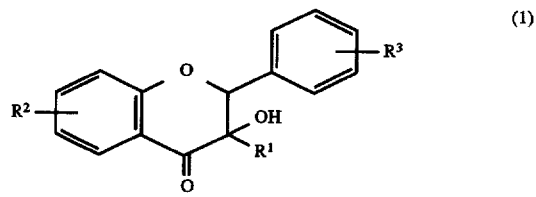

(1)

wherein $R^1$ represents an alkyl group, and each of $R^2$ and $R^3$ represents a hydrogen atom, an alkyl group which may have a substituent, an alkoxyl group which may have a substituent, a hydroxyl group, a cyano group, or a halogen atom.

The present invention also provides use of a flavanonol derivative represented by the above-described formula (1) as a hair-nourishing and hair-growing agent.

The present invention further provides a method of nourishing and growing the hair, characterized by administering an effective amount of a flavanonol derivative represented by the above-described formula (1).

Of all the compounds of formula (1), those excepting the compounds in which $R^1$ is a methyl group and $R^2$ and $R^3$ are both hydrogen atoms are novel compounds which have not yet appeared in literature. Therefore, the present invention also provides a flavanonol derivative represented by the following formula (1a):

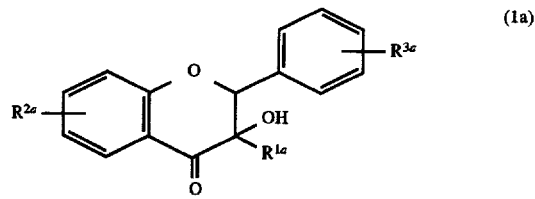

(1a)

wherein $R^{1a}$ represents a C1–C12 alkyl group, and each of $R^{2a}$ and $R^{3a}$ represents a hydrogen atom, a C1–C12 alkyl group which may be substituted by a halogen atom, a C1–C12 alkoxyl group which may be substituted by a C1–C12 alkoxyl group, a hydroxyl group, a cyano group, or a halogen atom; provided that $R^{1a}$ is not a methyl group when $R^{2a}$ and $R^{3a}$ are both hydrogen atoms.

BEST MODE FOR CARRYING OUT THE INVENTION

In the compounds of formula (1), synthesis examples have been reported with respect to each of a compound in which $R^2$ and $R^3$ are hydrogen atoms and $R^1$ is a methyl group, and the other compound in which $R^1$ is a methyl group, $R^2$ is a hydrogen atom, and a methoxy group is bound to each of the 3'- and 4'- positions [D. M. X. Donnelly, et al., Tetrahedron Lett., 1023, 1967; W. P. Cullen, et al., J. Chem. Soc. (C), 2848, 1971]. However, it is not known as to whether these compounds have hair-nourishing or hair-growing effects.

In the above formula (1) representing the flavanonol derivative which is used as the active ingredient of the hair-nourishing and hair-growing agent of the present invention, alkyl groups represented by $R^1$ are preferably C1–C12 linear or branched alkyl groups, still more preferably C1–C8 linear or branched alkyl groups, particularly preferably C1–C5 linear or branched alkyl groups, and most preferably a methyl group and an ethyl group.

Examples of alkyl groups which may have substituents and which are represented by $R^2$ or $R^3$ include C1–C12 linear or branched alkyl groups which may each be substituted by 1–3 members selected from the group consisting of a halogen atom, a hydroxyl group, and an amino group. Of such alkyl groups, preferable ones are C1–C12 (more preferably C1–C8, and still more preferably C1–C5) linear or branched alkyl groups which may each be substituted by 1–3 halogen atoms. Specific examples of such alkyl groups which may have substituents include methyl, ethyl, n-propyl, isopropyl, n-butyl, tert-butyl, n-pentyl, and trifluoromethyl. Examples of alkoxyl groups which may have substituents include C1–C12 alkoxyl groups which may each be substituted by a C1–C12 alkoxyl group or by a hydroxyl group. Of such alkoxyl groups, those particularly preferred are C1–C12 alkoxyl groups which may each be substituted by a C1–C12 alkoxyl group. C1–C6 alkoxyl groups which may each be substituted by C1–C6 alkoxyl group are particularly preferred. Specific examples of such alkoxyl groups which may have substituents include methoxy, ethoxy, n-propoxy, isopropoxy, n-butoxy, n-pentyloxy, methoxymethoxy, 2-ethoxyethoxy, and 2-methoxyethoxy. Examples of halogen atoms include fluorine, bromine, chlorine, and iodine.

Since a flavanonol derivative (1) has an asymmetric carbon atom at each of the 2- and 3- positions, the derivative may take a plurality of stereoisomers. The present invention encompasses all possible stereoisomers and mixture of stereoisomers. Stereoisomers are referred to as trans-isomers or cis-isomers, according to the relation between the aromatic ring at the 2- position and the hydroxyl group at the 3- position. In the present invention, trans-isomers are particularly preferred.

Flavanonol derivatives (1) may be prepared, for example, via the following reaction scheme:

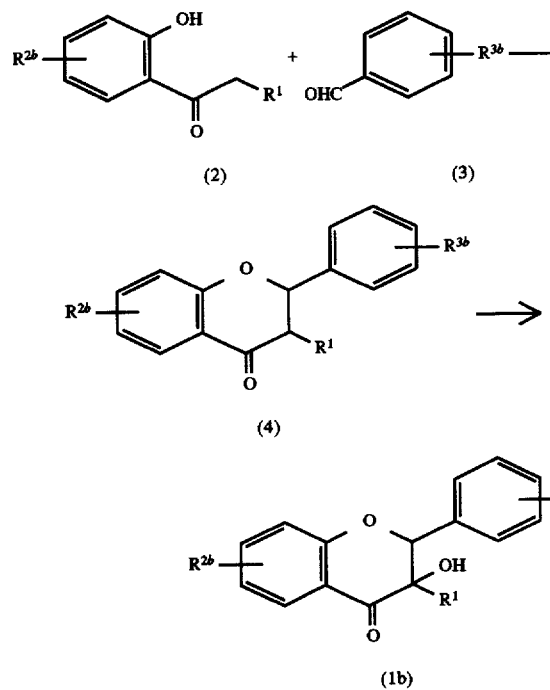

(wherein each of $R^{2b}$ and $R^{3b}$ represents a hydrogen atom, an alkyl group which may have a substituent, an alkoxyl group which may have a substituent, a cyano group, or a halogen atom; and $R^{1a}$ has the same meaning as defined before).

Briefly, an o-hydroxyacyl benzene (2) reacts with a benzaldehyde (3) to afford a flavanone (4), which reacts with an oxidizer to produce a flavanonol (1b).

The reaction of o-hydroxyacyl benzene (2) and benzaldehyde (3) proceeds, for example, through stirring, while applying heat, (2) and (3) in alcohol together with acetic acid and pyrrolidine. It is also possible to stir, while applying heat, (2) and (3) in hydrated dimethylformamide in the presence of a base such as sodium hydroxide.

It is preferred that the reaction of flavanone (4) and an oxidizer be performed, for example, in hydrated alcohol and in the presence of a base such as sodium hydroxide. Oxidizers are preferably hydrogen peroxide and peracids such as perbenzoic acid.

Of the compounds represented by formula (1), those in which $R^2$ or $R^3$ or both represents a hydroxyl group may be prepared, for example, by hydrolyzing a compound of formula (1b) in which $R^{2b}$ or $R^{3b}$ or both represents an alkoxyalkoxy group. The hydrolysis may proceed, for example, through stirring with heat to react the methoxymethoxy derivative with 3 N HCl in alcohol.

Of the compounds represented by formula (1), those in which $R^2$ or $R^3$ or both represents an alkoxyl group may be prepared in accordance with the above reaction scheme. They may also be prepared through O-alkylation of compounds in which $R^2$ or $R^3$ or both represents a hydroxyl group. O-Alkylation may proceed, for example, through reacting a base such as potassium carbonate with alkyl halide in a polar solvent such as dimethylformamide.

In order to obtain trans-isomers of flavanonol derivatives (1) in a selective fashion, it is a preferable practice that isomers are separated through recrystallization, etc. after flavanones (4) are synthesized, and that the isomers are subjected to oxidation.

The flavanonol derivatives (1) directly act on hair matrix cells to cause differentiation and proliferation, act to accelerate growth of hair shafts, and exhibit strong hair-nourishing effects. Therefore, they can be used as active ingredients of hair-nourishing and hair-growing compositions. They may preferably incorporated in hair-nourishing and hair-growing compositions in amounts of 0.0001–10% by weight, and preferably in amounts of 0.001–3% by weight.

Although flavanonol derivatives (1) may be used singly, they may also be used in combination with blood-flow accelerators, antibacterial agents, keratolytic agents agents, anti-seborrheal agents, local stimulators, antiinflammation agents, humectants, anti-androgen agents, follicle activating agents, etc. for the purpose of reinforcing the hair-nourishing effects of the derivatives. Since these agents do not act directly on the hair and act through mechanisms different from those of flavanonol derivatives (1), stronger hair-growing effects are exhibited when they are co-used. For example, blood flow accelerators accelerate supply of nutrients to hair matrix cells and transportation of metabolites from hair matrix cells, thereby indirectly accelerating growth of the hair. Antibacterial agents suppress bacterial actions to the scalp, thereby also indirectly accelerating growth of the hair.

Of these ingredients, examples of blood-flow accelerators include acetylcholine, swertia extracts, ginseng extracts, gingko extracts, calpronium chloride, diphenhydramine hydrochloride, gamma-oryzanol, sacretin, chromacalim, cepharantin, nicorandil, vitamin E, vitamin E derivatives such as vitamin E nicotinate, pinacidil, minoxidil, phthalides, quina extracts, Japanese iris root extracts, orange peel extracts, and citron extracts. Of these, preferable ones are acetylcholine, ginseng extracts, gingko extracts, vitamin E and its derivatives, cepharantin, minoxyzyl, calpronium chloride, diphenhydramine hydrochloride, gamma-oryzanol, sacretin, chromacarim, cepharantin, nicorangyl, pinacydyl, minoxyzyl, phthalides, quina extracts, Japanese iris root extracts, orange peel extracts, and citron extracts. It is particularly preferred to use swertia extracts, ginseng extracts, gingko extracts, vitamin E and its derivatives, cepharantin, minoxyzyl, calpronium chloride, and phthalides.

Examples of antibacterial agents include isopropylmethyl phenol, benzalconium chloride, octopirox, sensitive dye 101, sensitive dye 201, chlorohexidine, salicylic acid, zinc pyrithione, potassium sorbate, biozole, hinokitiol, and phenol. Examples of local stimulators include camphor, 1-menthol, vanilyl amide nonylate, ginger tincture, Holland mustard extracts, cantharis tincture, zanthoxylum fruit extracts, mentha herb oil, horseradish extracts, etc. Of these agents, preferable ones are octopirox, benzalconium chloride, zinc pyrithione, salicylic acid, and isopropylmethyl phenol.

Examples of keratolytic agents include aspirin. Examples of antiseborrheal agents include sulfur, thioxolon, banside, polysorbates, lecithin, and cashew extracts.

Examples of anti-inflammation agents include azulene, guaiazulene, antihistaminic agents (such as diphenhydramine), hydrocortisone acetate, predonisolone, scutellaria root extracts, camomile extracts, artemisia capillaris extracts, platycodon root extracts, apricot kernel extracts, gardenia extracts, sasa veitchii extracts, gentianae extracts, symphytum officinale extracts, crataegus cuneata extracts, white birch extracts, galinsoga ciliata extracts, malva sylvestris extracts, peach kernel extracts, peach-leaf extracts, and eriobotrya japonica extracts.

Examples of humectants include hypericum erectum, soluble collagen, glycerol, chondroitin sulfate, tuberose polysaccharides, plant worm, trisaccharides, urea, biohyaluronic acid, hyaluronic acid, vitamin C phosphate calcium salt, sodium pyrrolidone carbonate, propylene glycol, isodonis herba extracts, hordeum vulgare extracts, orange extracts, sea-weed extracts, cucumber extracts, arctium extracts, shiitake-mushroom extracts, rehmannia root extracts, duke extracts, eriobotrya japonica extracts, grape-leaf extracts, prune extracts, luffa aegyptiaca extracts, rosa odorata extracts, minisasanishiki, lily extracts, and apple extracts.

Examples of anti-androgen agents include ethinyl estradiol, chlormadinone acetate, etc.

Examples of follicle activators include N-acetyl-L-methionine, disodium adenosine triphosphate, potassium aspartate, sensitive dye 301, pentadecanoic glyceride, netakanal, ethyl pantothenate, panthenol, biotin, sodium mononitroguayacol, yeast extracts, pearl protein extracts, jujube extracts, panax rhizome, garlic components, placenta extracts, and royal jelly extracts.

Active ingredients other than flavanonol derivatives (1) are preferably used as a mixture of one, two, or more species. Moreover, they are preferably used after dissolved in water or in a solvent consisting of water and lower alcohol. They are preferably incorporated in the hair-nourishing and hair-growing composition of the present invention in amounts of 0.001–5% by weight, and particularly preferably 0.01–3% by weight, from the viewpoints of synergetic effects expected when they are used in combination with flavanonol derivatives (1) and of stimulative sensation on the scalp.

The hair-nourishing and hair-growing compositions of the present invention primarily take the liquid form. They are typically formed into lotions, but they may also be prepared in the form of creams and gels. When liquids are formed, it is particularly preferred that they contain carbon dioxide gas.

It is known that, when carbon dioxide gas is dissolved in a solution having an acidic pH, it is present as $CO_2$ molecules in the solution, thereby exhibiting a vasodilation action. Therefore, liquids of hair-nourishing and hair-growing compositions are preferably adjusted to have a pH of 7 or less, and particularly preferably between pH 4.5 and 6.5. When carbon dioxide gas is pressurized in a hair-nourishing and hair-growing composition and is dissolved therein, the pH of the composition decreases. In this case, the ultimate pH is adjusted to fall within the mentioned ranges. Examples of pH regulators which are preferably used include organic acids such as citric acid, tartaric acid, and lactic acid, salts of organic acids, phosphoric acid, and salts of phosphoric acid.

In order to incorporate carbon dioxide gas into hair-nourishing and hair-growing compositions of the present invention, a variety of methods may be used. In one method, all components excepting carbon dioxide gas are placed in a pressure-resistant container, and carbon dioxide gas is sealed in the container at a high pressure. In another method, a component which contains a carbonate such as sodium hydrogencarbonate and is thus capable of emitting carbon dioxide gas is placed in a pressure-resistant container, a pH regulator is added thereto to generate carbon dioxide gas, after which the container is immediately sealed. In still another method, dry ice pellets are placed in a container and sealed. Of these methods, the method involving sealing highly pressurized carbon dioxide gas is preferred.

By performing such a method, carbon dioxide gas is partly dissolved and incorporated in the hair-nourishing and hair-growing composition of the present invention, and is partially present in the container in a gaseous state. In the present invention, it is important that carbon dioxide gas be incorporated in the hair-nourishing and hair-growing composition in a dissolved state. The amount of carbon dioxide gas thus incorporated in the composition is preferably not less than 60 ppm in terms of the concentration of carbon dioxide gas. Lower amounts cannot yield sufficient effects expected from the addition of carbon dioxide gas. The amounts of carbon dioxide gas may be adjusted by changing the amounts of carbon dioxide gas which is injected (added with pressure). Under general circumstances, it is preferred that the interior pressure of the container be adjusted to be 1.2–8 $kg/cm^2$ (gauge pressure) at 35° C.

The hair-nourishing and hair-growing composition of the present invention may contain, in addition to the above ingredients, suitable amounts of oily bases, gelling agents, a variety of emulsifiers, perfumes, antioxidants such as parahydroxybenzoic esters, and colorants such as a dye.

The hair-nourishing and hair-growing composition of the present invention may be prepared through processing the aforementioned essential components and optional components using conventional methods, i.e., performing operations such as mixing.

EXAMPLES

The present invention will next be described by way of example, which should not be construed as limiting the invention.

Synthesis Example 1 trans-3,4'-Dimethylflavanonol

A mixture of 2'-hydroxypropiophenone (15.0 g, 0.10 mol), 4-methylbenzaldehyde (13.2 g, 0.11 mol), piperidine (20.0 ml, 0.20 mol), and acetic acid (10.0 ml, 0.17 mol) was stirred while refluxing with heat in ethanol (100 ml) for 18 hours under nitrogen. After the solvent was evaporated, water (300 ml) was added to obtain crude crystals, which were recrystallized from hexane: ethyl acetate, thereby obtaining trans-3,4'-dimethylflavanone (23.5 g, 93.3 mmol, 93%). Into a mixture of trans-3,4'-dimethylflavanone (2.52 g, 10.0 mol) and sodium hydroxide (3.20 g, 80.0 mmol) contained in a solvent mixture of ethanol (20 ml) - water (60 ml), 30% hydrogen peroxide solution in water (6.80 g, 60.0 mol) was added dropwise. The resultant mixture was stirred at 40° C. Seventy-two (72) hours later, water (100 ml) was added and cooled on ice. Precipitates were collected through filtration, thereby obtaining crude crystals. The crude crystals were subjected to silica gel column chromatography ($SiO_2$ 300 g, hexane: ethyl acetate), then recrystallization from hexane: ethyl acetate, to obtain trans-3,4'-dimethylflavanonol (1.61 g, 6.0 mmol, 60%).

Colorless fine crystals, mp. 104.9°–105.4° C.

IR(KBr, $cm^{-1}$) 3492, 2996, 1694, 1612, 1468, 1310, 1274, 1178, 1014, 966, 770.

¹H-NMR(CDCl₃, δppm) 1. 19 (s, 3H), 2. 39 (s, 3H), 3. 72 (s, 1H), 5. 26 (s, 1H), 7. 10 (d, 2H, J=8. 1 Hz), 7. 12~7. 22 (m, 2 H), 7. 48 (d, 2H, J=8. 1 Hz), 7. 53~7. 61 (m, 1H), 7. 94 (dd, 1H, J=8. 1, 1. 6 Hz).

Reactions similar to those described in Synthesis Example 1 were performed using appropriate aldehydes, thereby obtaining the compounds described in Synthesis Examples 2 through 12 below.

Synthesis Example 2
trans-4'-Ethyl-3-methylflavanonol
Colorless fine crystals, mp. 130.5°–131.3° C.
IR(KBr, cm⁻¹) 3484, 1692, 1610, 1466, 1308, 1234, 1018.
¹H-NMR (CDCl₃, δppm) 1. 21 (s, 3H), 1. 27 (t, 3H, 7. 6 Hz), 2. 2H, J=7. 6 Hz), 3. 74 (bs, 1H), 5. 27(s, 1H), 7. 08~7. 15(m, 2H), 7. 27(d, 2H, J=8. 1 Hz), 7. 50(d, 2H, J=8. 1 Hz), 7. 50~7. 62 (m, 1H), 7. 94 (dd, 1H, J=8. 1, 8. 1 Hz)

Synthesis Example 3
cis-4'-Butyl-3-methylflavanonol
Colorless fine crystals, mp. 112.7°–113.3° C.
IR (KBr, cm⁻¹) 3536, 2956, 2872, 1688, 1612, 1466, 1296, 1234, 766.
¹H-NMR (CDCl₃, δppm) (t, 3H, J=7. 2 Hz), 1. 23~1. 42 (m, 2H), 1.49~1. 64 (m, 5H), 2. 58 (t, 2H, J=7. 4 Hz), 2. 99 (s, 1H), 5. 31 (s, 1H), 7. 01~7. 11 (m, 2H), 7. 11 (d, 2H, J=8. 2 Hz), 7. 25 (d, 2H, J=8. 2 Hz), 7. 50~7. 58 (m, 1H), 7. 89 (dd, 1H, J=7. 8, 1.7 Hz).

Synthesis Example 4
trans-4'-Butyl-3-methylflavanonol
Colorless fine crystals, mp. 88.5°–89.3° C.
IR (KBr, cm⁻¹) 3476, 2960, 2860, 1684, 1610, 1470, 1312, 1234, 1014, 758.
¹H-NMR (CDCl₃, δppm) 0. 94 (t, 3H, J=7.2 Hz), 1. 21 (s, 3H), 1. 29~1. 47 (m, 2H), 1. 52~1. 70 (m, 2H), 2. 65 (t, 2H, J=7. 9 Hz), 3. 74 (s, 1H), 5. 27 (s, 1H), 7. 07~7. 15 (m, 2H), 7. 25 (d, 2H, J=8. 0 Hz), 7. 49 (d, 2H, J=8. 0 Hz), 7. 52~7. 61 (m, 1H), 7. 94 (dd, 1H, J=8. 0, 1. 8 Hz).

Synthesis Example 5
trans-3'-Methyl-4'-methoxyflavanonol
Colorless fine crystals, mp. 119.3°–119.8° C.
IR(KBr, cm⁻¹) 3480, 2988, 2940, 2868, 2844, 1690, 1610, 1518, 1470, 1312, 1252, 1228, 1180, 1030, 1014, 908, 776.
¹H-NMR (CDCl₃, δppm) 1. 20 (s, 3H), 3. 74 (s, 1H), 3. 85 (s, 3H), 5. 24(s, 1H), 6. 97 (d, 2H, J=8. 9 Hz), 7. 05~7. 15 (m, 2H), 7. 52 (d, 2H, J=8. 9 Hz), 7. 54~7. 62 (m, 1H), 7. 94(dd, 1H, J=8. 3, 1. 7 Hz)

Synthesis Example 6
trans-4'-Propoxy-3-methylflavanonol
Colorless fine crystals, mp. 137.2°–138.1° C.
IR(KBr, cm⁻¹) 3496, 2964, 2880, 1692, 1616, 1466, 1250, 1236, 1182, 752.
¹H-NMR(CDCl₃, δppm) 1. 05(t, 3H, J=7. 5 Hz), 1. 20 (s, 3H), 1. 20~1. 56 (m, 2H), 3. 72 (s, 1H), 3. 96 (t, 2H, J=6. 6 Hz), 5. 24 (s, 1H), 6. 96 (d, 2H, J=8. 8 Hz), 7. 02~7. 15 (m, 2 H), 7. 49(d, 2H, J=8. 8 Hz), 7. 52~7. 61 (m, 1H), 7. 93 (dd, 1H, J=8. 0, 1. 7 Hz)

Synthesis Example 7
trans-4'-Chloro-3-methylflavanonol
Colorless fine crystals, mp. 112.1°–112.6° C.
IR(KBr, cm⁻¹) 3492, 2988, 2896, 1692, 1610, 1496, 1470, 1306, 1230, 1182, 1014, 966, 758.
¹H-NMR(CDCl₃,δppm) 1. 16 (s, 3H), 3. 79 (s, 1H), 5. 27 (s, 1H), 7. 09~7. 18(m, 2H), 7. 41 (d, 2H, J=8. 6 Hz), 7. 53~7. 63 (m, 3H), 7. 94 (dd, 1H, J=8. 8, 1. 5 Hz)

Synthesis Example 8
trans-3'-Chloro-3-methylflavanonol
Colorless fine crystals, mp. 102.9°–103.3° C.
IR (KBr, cm⁻¹) 3460, 1696, 1610, 1466, 1306, 1224, 1022, 798, 758, 704.
¹H-NMR (CDCl₃, δppm) 1. 18 (s, 3H), 3. 81 (s, 1H), 5. 26 (s, 1H), 7. 09~7. 18 (m, 2H) 7. 35~7. 64 (m, 5H), 7. 94 (dd, 1H, J=7. 8, 1. 9 Hz).

Synthesis Example 9
trans-2'-Chloro-3-methylflavanonol
Colorless fine crystals, mp. 171.6°–172.6° C.
IR (KBr, cm⁻¹) 3468, 3080, 2992, 2940, 1684, 1606, 1476, 1468, 1306, 1230, 1150, 1098, 1016, 760, 736.
¹NMR (CDCl₃, δppm) 1. 32 (s, 3H), 3. 62 (s, 1H), 5. 89 (s, 1H), 7. 05~7. 18 (m, 2H), 7. 34~7. 61 (m, 4H), 7. 78~7. 81 (m, 1H), 7. 97 (dd, 1H, J=7. 8, 1. 8 Hz).

Synthesis Example 10
trans-4'-Cyano-3-methylflavanonol
Colorless fine crystals, mp. 194.5°–195.1° C.
IR(KBr, cm⁻¹) 3484, 3316, 1690, 1662, 1610, 1476, 1308, 1232, 756.
¹H-NMR(CDCl₃, δppm) 1. 17 (s, 3H), 3. 84 (s, 1H), 5. 35 (s, 1H), 7. 10~7. 18 (m, 2H), 7. 56~7. 65 (m, 1H), 7. 71 (d, 2H, J=8. 4 Hz), 7. 89 (d, 2H, J=8. 4 Hz), 7. 95 (dd, 1H, J=7. 8, 1. 8 Hz).

Synthesis Example 11
trans-4'-Trifluromethyl-3-methylflavanonol
Colorless fine crystals, mp. 122.8°–123.5° C.
IR(KBr, cm⁻¹) 3496, 2992, 2904, 1694, 1610, 1470, 1332, 1110, 760.
¹H-NMR(CDCl₃, δppm) 1. 16 (s, 3H), 3. 84(s, 1H), 5. 35 (s, 1H), 7. 10~7. 19 (m, 2H), 7. 56~7. 65 (m, 1H), 7. 69 (d, 2H, J=8. 7 Hz), 7. 75 (d, 2H, J=8. 7 Hz), 7. 96 (dd, 1H, J=8. 8, 1. 5 Hz)

Synthesis Example 12
trans-3',4'-Dimethoxy-3-methylflavanonol
Colorless fine crystals, mp. 102.1°–102.7° C.
IR(KBr, cm⁻¹) 3480, 2980, 2876, 2848, 1696, 1610, 1520, 1470, 1224, 1140, 1024.
¹H-NMR(CDCl₃, δppm) 1. 22 (s, 3H), 3. 75(s, 1H), 3. 92 (s, 3H), 3. 94 (s, 3H), 5. 24 (s, 1H), 6. 94 (d, 1 H, J=8. 2 Hz), 7. 09~7. 19 (m, 4H), 7. 54~7. 62 (m, 1H), 7. 94 (dd, 1H, J=8. 0, 1. 6 Hz)

Synthesis Example 13
trans-6-Chloro-3-methylflavanonol
Into a mixture of p-chlorophenol (20.0 g, 156 mmol), pyridine (14.8 g, 187 mmol), and toluene (150 ml), propionic acid chloride (17.3 g, 187 mmol) was added dropwise, and the resultant mixture was stirred for 1 hour at room temperature. Water (150 ml) was added and the aqueous layer was discarded. The organic layer was concentrated and distilled under reduced pressure (bp. 73°–76° C./0.2 mmHg), thereby obtaining a propionic acid-p-chlorophenyl ester (25.6 g, 138 mmol, 89%).

Subsequently, the propionic acid-p-chlorophenyl ester (20.0 g, 108 mmol) and anhydrous aluminum chloride (27.5 g, 206 mmol) were mixed and the mixture was stirred for 15 minutes in a hot bath at a temperature of 180° C. After the mixture was cooled on ice, 1N HCl (400 ml) was added, and extraction was performed using methylene chloride. The solvent was evaporated from the extract. Recrystallization from hexane afforded 5-chloro-2-hydroxyphenylethylketone (16.7 g, 91 mmol, 84%).

5-Chloro-2-hydroxyphenylethylketone was subjected to a reaction similar to those described in Synthesis Example 1, thereby obtaining trans-6-chloro-3-methylflavanonol. Colorless fine crystals, mp. 92.0°–92.5° C.

IR (KBr, cm$^{-1}$) 3480, 1698, 1604, 1472, 1172, 1022.

$^1$H-NMR (DMSO-d$_6$, δppm) 1. 03 (s, 3H), 5. 43 (s, 1H), 5. 89 (s, 1H), 7. 22 (d, 1H, J=8. 8 Hz), 7. 39–7. 52 (m, 5H), 7. 68 (dd, 1H, J=8. 8, 2. 7 Hz), 7. 77 (d, 1H, J=2. 7 Hz).

Reactions similar to those described in Synthesis Examples 1 and 13 were performed using appropriate starting materials, thereby obtaining the compounds described in Synthesis Examples 14 through 22.

Synthesis Example 14 cis-3,6-Dimethylflavanonol

Colorless fine crystals, mp. 112.5°–113.5° C.

IR(KBr, cm$^{-1}$) 3448, 1680, 1622, 1496, 1300, 1224, 1146, 1018, 758, 696.

$^1$H-NMR(DMSO-d$_6$, δppm) 1. 07 (s, 3H),2. 31 (s, 3H), 5. 25 (s, 1H),5. 89(s, 1H), 6. 96 (d, 1H, J=8. 4 Hz) , 7. 37–7. 43 (m, 4 H) , 7. 53–7. 58 (m, 2 H) , 7. 62 (d, 1H, J=1. 7 Hz)

Synthesis Example 15 trans-3,6-Dimethylflavanonol

Colorless fine crystals, mp. 145.5°–146.5° C.

IR (KBr, cm$^{-1}$) 3468, 1684, 1618, 1492, 1298, 1224, 1148, 1128.

$^1$H-NMR (DMSO-d$_6$, δppm) 1. 01 (s, 3H), 2. 32 (s, 3H), 5. 32 (s, 1H), 5. 73 (s, 1H), 7. 05 (d, 1H, J=8. 4 Hz), 7. 38–7. 52 (m, 6H), 7. 63 (d, 1H, J=1. 8 Hz)

Synthesis Example 16 cis-7-Chloro-3-methylflavanonol

Colorless fine crystals, mp. 95.0°–96.0° C.

IR (KBr, Cm$^{-1}$) 3460, 1688, 1602, 1430, 1218, 1016, 742, 696.

$^1$H-NMR (DMSO-d$_6$, δppm) 1. 06 (s, 3H), 5. 40 (s, 1H), 6. 03 (s, 1H), 7. 18 (dd, 1H, J=8. 3, 1. 8 Hz), 7. 24 (d, 1H, J=1. 8 Hz), 7. 39–7. 58 (m, 5H), 7. 84 (d, 1H, J=8. 3 Hz).

Synthesis Example 17 trans-7-Chloro-3-methylflavanonol

Colorless fine crystals, mp. 65.5°–67.5° C.

IR(KBr, cm$^{-1}$) 3480, 1690, 1604, 1430, 1218, 1020.

$^1$H-NMR(DMSO-d$_6$, δppm) 1. 03 (s, 3H), 5. 44 (s, 1H), 5. 85 (s, 1H), 7. 22 (dd, 1H, J=8. 4, 1. 9 Hz), 7. 31 (d, 1H, J=1. 9 Hz), 7. 38–7. 51 (m, 5H), 7. 84 (d, 1H, J=8. 4 Hz)

Synthesis Example 18 trans-3,7-Dimethylflavanonol

Colorless fine crystals, mp. 92.0°–92.5° C.

IR (KBr, cm$^{-1}$) 3468, 1684, 1618, 1494, 1456, 1248, 1154, 1120, 1028, 744, 698.

$^1$H-NMR (DMSO-d$_6$, δppm) 1. 00 (s, 3H), 2. 35 (s, 3H) , 5. 33 (s, 1H), 5. 71 (s, 1H), 6. 97 (s, 1H), 6. 98 (d, 1H, J=8. 5 Hz), 7. 37–7. 52 (m, 5H), 7. 72 (d, 1 H, J=8. 5 Hz).

Synthesis Example 19 trans-3-Ethylflavanonol

Colorless fine crystals, mp. 100.2°–100.7° C.

IR(KBr, cm$^{-1}$) 3488, 2972, 2940, 2880, 1692, 1620, 1468, 1328, 1276, 1224, 1024, 766, 700.

$^1$H-NMR(CDCl$_3$, δppm) 0. 66 (t, 3H, J=7. 5 Hz), 1. 45–1. 94 (m, 2H), 3. 92 (s, 1H), 5. 36 (s, 1H), 7. 08–7. 15 (m, 2H), 7. 37–7. 63 (m, 6H), 7. 92 (dd, 1H, J=8. 1, 1. 7 Hz).

Synthesis Example 20 trans-3-Octylflavanonol

Yellow oil

IR(neat, cm$^{-1}$) 3496, 3040, 2982, 2860, 1694, 1612, 1470, 1324, 1296, 1226, 1014, 756, 696.

$^1$H-NMR (CDCl$_3$, δppm) 0. 81(t, 3H, J=7. 3 Hz), 1. 10–1. 88 (m, 14H), 3. 93(s, 1H), 5. 32(s, 1H), 7. 03–7. 16 (m, 2H) , 7. 35–7. 66 (m, 6H) , 7. 91 (dd, 1H. J=8. 0, 1. 8 Hz).

Synthesis Example 21 trans-8-Chloro-methylflavanonol

Colorless fine crystals, mp. 86.7°–87.9° C.

IR(KBr, cm$^{-1}$) 3464, 1704, 1602, 1472, 1446, 1248, 1136, 1022.

$^1$H-NMR (CDCl$_3$, δppm) 1. 18 (m, 3H), 3. 75 (s, 1H), 5. 37 (s, 1H), 7. 03–7. 11 (m, 1H), 7. 40–7. 50 (m, 3H), 7. 62–7. 68 (m, 3H), 7. 86 (dd, 1H, J=7. 9, 1. 6 Hz).

Synthesis Example 22 trans-3,7,4'-Trimethylflavanonol

Yellow oil

IR (neat, cm$^{-1}$) 3496, 3016, 2988, 2928, 2872, 1690, 1620, 1456, 1238, 1186, 1154, 1040, 818, 752.

$^1$H-NMR (CDCl$_3$, δppm) 1. 17 (s, 3H), 2. 39(s, 3H) , 2. 40 (s, 3H), 3. 74 (s, 1H), 5. 23 (s, 1H), 6. 91–6. 95 (m, 2H), 7. 24 (d, 2H, J=8. 1 Hz), 7. 47 (d, 2H, J=8. 1 Hz), 7. 82 (d, I H, J=8. 4 Hz).

Synthesis Example 23 trans-7-Methoxymethoxy-3-methylflavanonol

N,N-diisopropylethylamine (40.1 g, 0.31 mol) was added to 2',4'-dihydroxypropylphenone (46.5 g, 0.28 mol) in methylene chloride (500 ml). To the resultant mixture, chloromethylmethyl ether (25.0 g, 0.31 mol) was added dropwise over 30 minutes while cooling with ice. The temperature of the system was gradually returned to room temperature and the mixture was stirred for 1 hour. Water (300 ml) was added for separating layers. The organic layer was concentrated, and then subjected to silica gel column chromatography (SiO$_2$ 700 g, hexane: ethyl acetate), thereby affording 2'-hydroxy-4'-(methoxymethoxy)propiophenone (52.5 g, 0.25 mol, 89%).

Subsequently, reactions similar to those described in Synthesis Example 1 were carried out using the 2'-hydroxy-4'-(methoxymethoxy)-propiophenone and appropriate aldehydes, to obtain trans-7-methoxymethoxy-3-methylflavanonol.

Colorless fine crystals, mp. 104.0°–106.4° C.

IR(KBr, cm$^{-1}$) 3464, 3092, 2964, 1686, 1612, 1450, 1252, 1150, 1104, 1072, 1014, 766, 730.

$^1$H-NMR(CDCl$_3$, δppm) 1. 18(s, 3H), 3. 50 (s, 3H), 3. 80(s, 1H), 5. 24 (s, 2H), 5. 28(s, 1H), 6. 70–6. 80 (m, 2H), 7. 40–7. 65(m, 5H), 7. 88 (d,1H, J=8. 6 Hz)

Synthesis Example 24 trans-7-Methoxymethoxy-3,4'-dimethylflavanonol

Reactions similar to those described in Synthesis Example 1 were carried out using 2'-hydroxy-4'-(methoxymethoxy)-propiophenone obtained in Synthesis Example 23 and appropriate aldehydes, thereby obtaining the target compound.

Colorless fine crystals, mp. 139.9°–140.7° C.

IR(KBr, cm$^{-1}$) 3480, 2980, 2924, 1684, 1610, 1454, 1252, 1142, 1000.

$^1$H-NMR(CDCl$_3$, δppm) 1. 17(s 3H) , 2. 39 (s, 3H) , 3. 49(s 3H) , 3. 75 (s, 1H), 5. 23(s 3H), 6. 72–6. 79 (m, 2H) , 7. 23(d 2H, J=8. 2 Hz), 7. 46(d 2H, J=8. 2 Hz), 7. 87(d 1H, J=8. 6 Hz)

Synthesis Example 25 trans-4'-Methoxymethoxy-3-methylflavanonol

Reactions similar to those described in Synthesis Example 23 were carried out using 4'-hydroxybenzaldehyde, thereby obtaining 4'-methoxymethoxy-benzaldehyde. The procedure of Synthesis Example 1 was repeated to obtain the target compound.

Colorless fine crystals, mp. 100.5°–101.2° C.

IR (KBr, cm$^{-1}$) 3476, 2952, 1690, 1612, 1516, 1468, 1308, 1232, 1152, 986, 752.

$^1$H-NMR (CDCl$_3$, δppm)

1. 20 (s, 3H), 3. 50(s, 3H), 3. 74(s, 1H), 5. 23 (d, 2H, J=1. 9 Hz), 5. 25 (s, 1H), 7. 07–7. 15 (m, 4H), 7. 45–7. 61 (m, 3H), 7. 94(dd, 1H, J=7. 8, 2. 0 Hz).

Synthesis Example 26 trans-7-Hydroxy-3-methylflavanonol

7'-Methoxymethoxy-3-methylflavanonol (1.57 g, 5.0 mmol) and 4.3N HCl (28 ml) were put in ethanol (10 ml) and stirred for 1 hour at 50° C. The solvent was evaporated and extraction was performed using ethyl acetate. The solid matter obtained through silica gel column chromatography (SiO$_2$ 150 g, hexane: ethyl acetate) was recrystallized to obtain trans-7-hydroxy-3-methylflavanonol (1.13 g, 4.2 mmol, 84%).

Colorless fine crystals, mp. 169.3°–169.8° C.

IR (KBr, Cm$^{-1}$) 3396, 1682, 1606, 1470, 1372, 1278, 1244, 1104, 1028, 854, 758, 728. $^1$H-NMR (CDCl$_3$+DMSO-d$_6$, δppm) 1. 15 (s, 3H), 3. 93 (s, 1H), 5. 24 (s, 1H), 6. 51 (d, 1H, J=2. 2 Hz), 6. 62 (dd, 1H, J=2. 2, 8. 7 Hz), 7. 35–7. 60 (m, 5H), 7. 80 (d, 1H, J=8. 7 Hz), 9. 90 (bs, 1H)

The procedure of Synthesis Example 26 was repeated using trans-4'-methoxymethoxy-3-methylflavanonol or trans-7-methoxymethoxy-3,4'-dimethylflavanonol, thereby obtaining the compounds of Synthesis Examples 27 and 28.

Synthesis Example 27 trans-4'-Hydroxy-3-methylflavanonol

Colorless fine crystals, mp. 155.2°–155.7° C.

IR (KBr, cm$^{-1}$) 3524, 3444, 2932, 1690, 1614, 1520, 1470, 1228, 758. $^1$H-NMR (DMSO-d$_6$, δppm) 1. 03 (s, 3H), 5. 24 (s, 1H), 5. 66 (bs, 1H), 6. 78 (d, 2H, J=8. 6 Hz), 7. 08–7. 17 (m, 2H), 7. 27 (d, 2H, J=8. 6 Hz); 7. 57–7. 65 (m, 1H), 7. 81 (dd, 1H, J=7. 8, 1. 4 Hz) , 9. 49 (bs, 1H)

Synthesis Example 28 trans-7-Hydroxy-3,4'-dimethylflavanonol

Colorless fine crystals, mp. 222.0°–222.4° C.

IR (KBr, cm$^{-1}$) 3436, 1674, 1622, 1462, 1276, 1114.

$^1$H-NMR (DMSO-d$_6$, δppm) 0. 97 (s, 3H), 2. 33 (s, 3H) , 5. 22 (s, 1H), 5. 52 (s, 1H), 6. 34 (d, 1H, J=2. 2 Hz), 6. 57 (dd, 1H, J=8. 7, 2. 2 Hz), 7. 20 (d, 2H, J=8. 1 Hz), 7. 35 (d, 2H, J=8. 1 Hz), 7. 68 (d, 1H, J=8. 7 Hz).

Synthesis Example 29 trans-7-Methoxy-3-methylflavanonol trans-7-Hydroxy-3-methylflavanonol (0.54 g, 2.0 mmol) and potassium carbonate (0.41 g, 3.0 mmol) were added to acetone (20 ml). Iodomethane (0.57 g, 4.0 mmol) was further added, and the resultant mixture was stirred for 1 hour at 50° C. Extraction was performed using ethyl acetate. Silica gel column chromatography (SiO$_2$ 70 g, hexane: ethyl acetate) afforded trans-7-methoxy-3-methylflavanonol (0.57 g, 2.0 mmol, 100% ).

Colorless oil

IR (neat, cm$^{-1}$) 3840, 3068, 3040, 2984, 2940, 2844, 1684, 1440, 1260, 1098, 1026, 838, 724, 698.

$^1$H-NMR (CDCl$_3$, δppm) 1. 17 (s, 3H), 3. 83 (s, 1H), 3. 86 (s, 3H), 5. 29 (s, 1H), 6. 54 (d, 1H, J=2.3 Hz). 6. 68 (dd, 1H, J=8. 9, 2. 4 Hz), 7. 38–7. 61 (m, 5H), 7. 87 (d, 1H, J=8. 9 Hz).

Synthesis Examples 30

The procedure of Synthesis Example 5 was repeated using trans-7-hydroxy-3,4'-dimethylflavanonol, thereby obtaining trans-7-methoxy-3,4'-dimethylflavanonol.

Colorless fine crystals, mp. 117.4°–118.2° C.

IR(KBr, cm$^{-1}$) 3460, 2972, 2928, 1680, 1610, 1448, 1262, 1096, 1024.

$^1$H-NMR(CDCl$_3$, δppm) 1. 17 (s, 3H) , 2. 39 (s, 3H), 3. 77 (s, 1H), 3. 86(s, 3H), 5. 24 (s, 1H), 6. 53 (d, 1H, J=2. 3 Hz), 6. 67 (dd, 1H, J=8. 9, 2. 3 Hz), 7. 24 (d, 2H, J=8. 2 Hz), 7. 46 (d, 2H, J=8. 2 Hz), 7. 86 (d, 1H, J=8. 9 Hz).

Test Example 1

A newborn SD rat was subjected to surgical operation to remove hair follicle organs of its whiskers. The follicles were placed side by side on triangle grids put on the inner dish of a petri dish for organ culture (Falcon 3037) (5 follicles per dish). The peripheral portion of the petri dish was filled with phosphate buffer so as to maintain humidity. Flavanonol derivative (1) was added to a medium (RPMI 1640) so as to achieve an ultimate concentration of 0.1 nM, followed by culturing under an atmosphere containing 90% O$_2$ and 5% CO$_2$ at 31° C. Growth of hair was observed during passage of time. The results are shown in Table 1. The hair growth rates in Table 1 are relative values obtained on day 3 of culture, with the growth in a culture medium only (i.e., without addition) being taken as 100. As is clear from Table 1, the flavanonol derivative (1) of the present invention exhibited remarkable effects of accelerating growth of the hair shaft.

TABLE 1

| Compounds | Hair growth rate (%) |
| --- | --- |
| Synthesis Ex. 1 | 125 |
| Synthesis Ex. 2 | 114 |
| Synthesis Ex. 6 | 112 |
| Synthesis Ex. 7 | 122 |
| Synthesis Ex. 8 | 118 |
| Synthesis Ex. 9 | 111 |
| Synthesis Ex. 10 | 110 |
| Synthesis Ex. 11 | 113 |
| Synthesis Ex. 13 | 120 |
| Synthesis Ex. 15 | 111 |
| Synthesis Ex. 17 | 112 |
| Synthesis Ex. 18 | 122 |
| Synthesis Ex. 19 | 113 |
| Synthesis Ex. 20 | 110 |
| Synthesis Ex. 21 | 130 |
| Synthesis Ex. 22 | 131 |
| Synthesis Ex. 24 | 114 |
| Synthesis Ex. 25 | 112 |
| Synthesis Ex. 26 | 111 |
| Synthesis Ex. 28 | 117 |
| Synthesis Ex. 30 | 115 |

Test Example 2

The hair on the back of each C3H mouse (male, 7 weeks old) whose hair had been in a resting stage was carefully shaved using electrical clippers and an electrical razor over an area of 2×4 cm$^2$ so as not to damage the skin. Groups of mice, each consisting of 20 such mice, were provided. Twenty µl of flavanonol derivative (1) in 70% ethanol (0.05%) were applied to the shaved part of each mouse once per day. In order to observe the state of regeneration of the hair, the shaved part was photographed at a predetermined magnification. Using an image analyzer, the ratio of the area in which hair was regenerated ("area in which hair is regenerated"/"area shaved") was computed, thereby obtaining the hair-growth activity. Groups to which the solvent (70% ethanol) was solely applied are referred to as "groups to which a control product was applied."

The-hair growth activity (%) measured on day 20 of application of each sample are shown in Table 2. As is apparent from Table 2, use of flavanonol derivative (1) of the present invention resulted in remarkably accelerated hair growth as compared with the results obtained on groups to which a control product was applied. Also, the mice to which the flavanonol derivative (1) of the present invention was applied were all healthy and no adverse effects were observed on their skin.

TABLE 2

| Groups treated | Hair growth activity (%) |
| --- | --- |
| groups to which a control product was applied | 61.8 |
| Compound obtained in Synthesis Example 1 | 72.4 |
| Compound obtained in Synthesis Example 7 | 72.3 |
| Compound obtained in Synthesis Example 8 | 69.1 |

Formulation Example 1 Hair-nourishing composition

| | | % by weight |
| --- | --- | --- |
| A: | trans-3,4'-Dimethylflavanonol | 0.05 |
| | Polyoxyethylene hydrogenated castor oil | 0.8 |
| | Ethanol | 30.0 |
| B: | Calpronium chloride | 1.0 |
| | Sodium dodecyl sulfate | 0.12 |
| | Dodecylmethylamine oxide | 0.18 |
| | Isopropyl alcohol | 15.0 |
| | Benzyl alcohol | 15.0 |
| | Glycerol | 2.0 |
| | Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 2 Hair-nourishing composition

| | | % by weight |
| --- | --- | --- |
| A: | trans-3,4'-Dimethylflavanonol | 0.05 |
| | Polyoxyethylene hydrogenated castor oil | 0.8 |
| | Ethanol | 30.0 |
| B: | Ginseng extract | 1.0 |
| | Sodium dodecyl sulfate | 0.12 |
| | Dodecylmethylamine oxide | 0.18 |
| | Isopropyl alcohol | 15.0 |
| | Benzyl alcohol | 15.0 |
| | Glycerol | 2.0 |
| | Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 3 Hair tonic

| | | % by weight |
| --- | --- | --- |
| A: | trans-3,4'-Dimethylflavanonol | 0.05 |
| | Minoxyzyl | 1.0 |
| | Polyoxyethylene hydrogenated castor oil | 0.8 |
| | Ginger tincture | 1.0 |
| | Isopropyl methyl phenol | 0.05 |
| | Ethanol | 55.0 |
| B: | Glycerol | 2.0 |
| | l-menthol | 0.06 |
| | Lactic acid | suitable amount |
| | purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 4 Hair tonic

| | | % by weight |
| --- | --- | --- |
| A: | trans-3,4'-Dimethylflavanonol | 0.05 |
| | Cepharantin | 0.02 |
| | Polyoxyethylene hydrogenated castor oil | 0.8 |
| | Ginger tincture | 1.0 |
| | Isopropyl methyl phenol | 0.05 |
| | Ethanol | 55.0 |
| B: | Glycerol | 2.0 |
| | l-menthol | 0.25 |
| | Lactic acid | suitable amount |
| | Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 5 Hair cream

| | | % by weight |
| --- | --- | --- |
| A: | Liquid paraffin | 10.0 |
| | Squalene | 7.0 |
| | Jojoba oil | 3.0 |
| | Solid paraffin | 3.0 |
| | Polyoxyethylene cetyl ether | 2.0 |
| | Sorbitan sesquioleate | 1.0 |
| | Potassium hydroxide | 0.1 |
| B: | trans-3,4'Dimethylflavanonol | 0.05 |
| | Capsicum tincture | 0.05 |
| | Glycerol | 3.0 |
| | Ethyl paraben | 0.1 |
| | Purified water | suitable amount |

The components belonging to A are dissolved with heat. Separately, the components belonging to B are dissolved with heat. B is added to A, the resultant mixture is mixed uniformly while stirring, emulsified, and then cooled, thereby obtaining a hair cream.

Formulation Example 6 Hair treatment

| | | % by weight |
| --- | --- | --- |
| A: | Avocado oil | 5.0 |
| | Squalene | 5.0 |
| | Liquid paraffin | 10.0 |
| | Stearic acid | 3.0 |

Formulation Example 6 Hair treatment

| | | % by weight |
|---|---|---|
| | Glycerol monostearate | 3.0 |
| | Lanolin alcohol | 5.0 |
| B: | trans-3,7-Dimethylflavanonol | 0.05 |
| | Swertia extract | 1.0 |
| | 1,3-Butylene glycol | 5.0 |
| | Triethanolamine | 1.0 |
| | Methyl paraben | 0.2 |
| | Purified water | suitable amount |

The components belonging to A are dissolved with heat. Separately, the components belonging to B are dissolved with heat. B is added to A, the resultant mixture is mixed uniformly while stirring, emulsified, and then cooled, thereby obtaining a hair treatment.

Formulation Example 7 Hair shampoo

| | | % by weight |
|---|---|---|
| A: | trans-3,4'-Dimethylflavanonol | 0.05 |
| | Vitamin E | 0.05 |
| | Lauric acid diethanolamide | 2.0 |
| | Lauric acid | 0.5 |
| | Cationic polymer (Polymer JR400, Union Carbide) | 0.3 |
| | Polyoxyethylene lauryl ether | 20.0 |
| B: | Perfume | 0.2 |
| | Citric acid | 1.5 |
| | Methyl paraben | 0.1 |
| | Purified water | suitable amount |

The components belonging to A are uniformly stirred and dissolved. To the resultant solution, the components belonging to B which have been uniformly dissolved in advance are added gradually, thereby obtaining a hair shampoo.

Formulation Example 8 Hair rinse

| | | % by weight |
|---|---|---|
| A: | trans-3,7-Dimethylflavanonol | 0.05 |
| | Cetanol | 3.0 |
| | Propylene glycol | 2.0 |
| | Liquid paraffin | 0.5 |
| | Hydroxyethylcellulose (HEC Dicel SE-850) | 0.5 |
| B: | Glyceryl glycyrrhetinate | 0.1 |
| | Trimethylstearyl chloride ammonium | 1.0 |
| | Methyl paraben | 0.1 |
| | Citric acid | suitable amount |
| | Perfume | 0.2 |
| | Purified water | suitable amount |

The components belonging to A are uniformly stirred and dissolved. To the resultant solution, the components belonging to B which have been uniformly dissolved in advance are added gradually, thereby obtaining a hair rinse.

Formulation Example 9 Aerosol

| | | % by weight |
|---|---|---|
| A: | trans-3,7-Dimethylflavanonol | 0.05 |
| | Benzyl nicotinate | 0.01 |
| | Vitamin E acetate | 0.05 |
| | Cetanol | 1.2 |

Formulation Example 9 Aerosol

| | | % by weight |
|---|---|---|
| | Propylene glycol | 4.0 |
| | Ethanol | 8.0 |
| | Purified water | suitable amount |
| B: | Liquefied petroleum gas (propellant) | 4.0 |

The components belonging to A were uniformly mixed and put in a container. The container was charged with B via a conventional method, thereby obtaining an aerosol.

Formulation Example 10 Hair foam

| | | % by weight |
|---|---|---|
| A: | trans-3,7-Dimethylflavanonol | 0.05 |
| | Hinokitiol | 0.1 |
| | Cetanol | 1.2 |
| | Propylene glycol | 2.0 |
| | Dimethylsilicone oil | 2.0 |
| | Polyoxyethylene hydrogenated castor oil | 2.5 |
| | Liquid paraffin | 1.0 |
| | Polyvinylpyrrolidone | 0.5 |
| | Methyl paraben | 0.2 |
| | Ethanol | 10.0 |
| | Purified water | suitable amount |
| B: | Liquefied petroleum gas (propellant) | 4.0 |

The components belonging to A were uniformly mixed and put in a container. The container was charged with B via a conventional method, thereby obtaining a hair foam.

Formulation Example 11 Hair-nourishing composition

| | | % by weight |
|---|---|---|
| A: | trans-3,4'-Dimethylflavanonol | 0.05 |
| | Pentadecanoic acid glyceride | 1.0 |
| | Polyoxyethylene hydrogenated castor oil | 0.8 |
| | Ethanol | 30.0 |
| B: | Sodium dodecyl sulfate | 0.12 |
| | Dodecylmethylamine oxide | 0.18 |
| | Isopropyl alcohol | 15.0 |
| | Benzyl alcohol | 15.0 |
| | Glycerol | 2.0 |
| | Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 12 Hair-nourishing composition

| | | % by weight |
|---|---|---|
| A: | trans-3,7-Dimethylflavanonol | 0.05 |
| | Ethyl pantothenate | 1.0 |
| | Polyoxyethylene hydrogenated castor oil | 0.8 |
| | Ethanol | 30.0 |
| B: | Sodium dodecyl sulfate | 0.12 |
| | Dodecylmethylamine oxide | 0.18 |
| | Isopropyl alcohol | 15.0 |
| | Benzyl alcohol | 15.0 |
| | Glycerol | 2.0 |
| | Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 13 Hair tonic

| | | % by weight |
|---|---|---|
| A: | trans-3,4'-Dimethylflavanonol | 0.05 |
| | Polyoxyethylene hydrogenated castor oil | 0.8 |
| | Ginger tincture | 1.0 |
| | Isopropyl methyl phenol | 0.05 |
| | Ethanol | 55.0 |
| B: | Biotin | 1.0 |
| | Glycerol | 2.0 |
| | l-menthol | 0.25 |
| | Lactic acid | suitable amount |
| | Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 14 Hair tonic

| | | % by weight |
|---|---|---|
| A: | trans-3,7-Dimethylflavanonol | 0.05 |
| | Polyoxyethylene hydrogenated castor oil | 0.8 |
| | Ginger tincture | 1.0 |
| | Isopropyl methyl phenol | 0.05 |
| | Ethanol | 55.0 |
| B: | Ginseng extract | 1.0 |
| | Glycerol | 2.0 |
| | l-menthol | 0.25 |
| | Lactic acid | suitable amount |
| | Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 15 Aerosol

| | | % by weight |
|---|---|---|
| A: | trans-3,4'-Dimethylflavanonol | 0.05 |
| | Panax rhizome | 0.01 |
| | Vitamin E acetate | 0.05 |
| | Cetanol | 1.2 |
| | Propylene glycol | 4.0 |
| | Ethanol | 8.0 |
| | Purified water | suitable amount |
| B: | Liquefied petroleum gas (propellant) | 4.0 |

The components belonging to A were uniformly mixed and put in a container. The container was charged with B via a conventional method, thereby obtaining an aerosol.

Formulation Example 16 Hair-nourishing composition

| | | % by weight |
|---|---|---|
| A: | trans-3,7-Dimethylflavanonol | 0.05 |
| | Polyoxyethylene hydrogenated castor oil | 0.8 |
| | Ethanol | 30.0 |
| B: | Dipotassium glycyrrhizate | 0.1 |
| | Sodium dodecyl sulfate | 0.12 |
| | Dodecylmethylamine oxide | 0.18 |

-continued

Formulation Example 16 Hair-nourishing composition

| | % by weight |
|---|---|
| Isopropyl alcohol | 15.0 |
| Benzyl alcohol | 15.0 |
| Glycerol | 2.0 |
| Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 17 Hair tonic

| | | % by weight |
|---|---|---|
| A: | trans-3,4'-Dimethylflavanonol | 0.05 |
| | Polyoxyethylene hydrogenated castor oil | 0.8 |
| | Ginger tincture | 1.0 |
| | Isopropyl methyl phenol | 0.05 |
| | Ethanol | 55.0 |
| B: | Glycyrrhetinole acid | 0.1 |
| | Glycerol | 2.0 |
| | Lactic acid | suitable amount |
| | Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 18 Hair cream

| | | % by weight |
|---|---|---|
| A: | trans-3,7-Dimethylflavanonol | 0.05 |
| | Liquid paraffin | 10.0 |
| | Squalene | 7.0 |
| | Jojoba oil | 3.0 |
| | Solid paraffin | 3.0 |
| | Polyoxyethylene cetyl ether | 2.0 |
| | Sorbitan sesquioleate | 1.0 |
| | Potassium hydroxide | 0.1 |
| B: | Camomile extract | 1.0 |
| | Glycerol | 3.0 |
| | Ethyl paraben | 0.1 |
| | Purified water | suitable amount |

The components belonging to A are dissolved with heat. Separately, the components belonging to B are dissolved with heat. B is added to A, the resultant mixture is mixed uniformly while stirring, emulsified, and then cooled, thereby obtaining a hair cream.

Formulation Example 19 Hair treatment

| | | % by weight |
|---|---|---|
| A: | trans-3,4'-Dimethylflavanonol | 0.05 |
| | Avocado oil | 5.0 |
| | Squalene | 5.0 |
| | Liquid paraffin | 10.0 |
| | Stearic acid | 3.0 |
| | Glycerol monostearate | 3.0 |
| | Lanolin alcohol | 5.0 |
| B: | Peach-leaf extract | 1.0 |
| | 1,3-Butylene glycol | 5.0 |

Formulation Example 19 Hair treatment

| | % by weight |
|---|---|
| Triethanolamine | 1.0 |
| Methyl paraben | 0.2 |
| Purified water | suitable amount |

The components belonging to A are dissolved with heat. Separately, the components belonging to B are dissolved with heat. B is added to A, the resultant mixture is mixed uniformly while stirring, emulsified, and then cooled, thereby obtaining a hair treatment.

Formulation Example 20 Hair shampoo

| | | % by weight |
|---|---|---|
| A: | trans-3,7-Dimethylflavanonol | 0.05 |
| | Lauric acid diethanolamide | 2.0 |
| | Lauric acid | 0.5 |
| | Cationic polymer | 0.3 |
| | (Polymer JR400, Union Carbide) | |
| | Polyoxyethylene lauryl ether | 20.0 |
| B: | 1-Menthol | 0.25 |
| | Perfume | 0.2 |
| | Citric acid | 1.5 |
| | Methyl paraben | 0.1 |
| | Purified water | suitable amount |

The components belonging to A are uniformly stirred and dissolved. To the resultant solution, the components belonging to B which have been uniformly dissolved in advance are added gradually, thereby obtaining a hair shampoo.

Formulation Example 21 Hair-nourishing composition

| | | % by weight |
|---|---|---|
| A: | trans-3,4'-Dimethylflavanonol | 0.05 |
| | Polyoxyethylene hydrogenated castor oil | 0.8 |
| | Ethanol | 30.0 |
| B: | Benzalconium chloride | 0.1 |
| | Sodium dodecyl sulfate | 0.12 |
| | Dodecylmethylamine oxide | 0.18 |
| | Isopropyl alcohol | 15.0 |
| | Benzyl alcohol | 15.0 |
| | Glycerol | 2.0 |
| | Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 22 Hair tonic

| | | % by weight |
|---|---|---|
| A: | trans-3,7-Dimethylflavanonol | 0.05 |
| | Octopirox | 0.05 |
| | Polyoxyethylene hydrogenated castor oil | 0.8 |
| | Ginger tincture | 1.0 |
| | Isopropyl methyl phenol | 0.05 |
| | Ethanol | 55.0 |
| B: | Glycerol | 2.0 |
| | Lactic acid | suitable amount |
| | Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 23

| Hair cream | | % by weight |
|---|---|---|
| A: | trans-3,4'-Dimethylflavanonol | 0.05 |
| | Liquid paraffin | 10.0 |
| | Squalane | 7.0 |
| | Jojoba oil | 3.0 |
| | Solid paraffin | 3.0 |
| | Polyoxyethylene cetyl ether | 2.0 |
| | Sorbitan sesquioleate | 1.0 |
| | Potassium hydroxide | 0.1 |
| B: | Hinokitiol | 0.1 |
| | Glycerol | 3.0 |
| | Ethyl paraben | 0.1 |
| | Purified water | suitable amount |

The components belonging to A are dissolved with heat. Separately, the components belonging to B are dissolved with heat. B is added to A, the resultant mixture is mixed uniformly while stirring, emulsified, and then cooled, thereby obtaining a hair cream.

Formulation Example 24

| Hair-nourishing composition | | % by weight |
|---|---|---|
| A: | trans-3,7-Dimethylflavanonol | 0.05 |
| | Polyoxyethylene hydrogenated castor oil | 0.8 |
| | Ethanol | 30.0 |
| B: | Thioxolon | 0.1 |
| | Sodium dodecyl sulfate | 0.12 |
| | Dodecylmethylamine oxide | 0.18 |
| | Isopropyl alcohol | 15.0 |
| | Benzyl alcohol | 15.0 |
| | Glycerol | 2.0 |
| | Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 25

| Hair tonic | | % by weight |
|---|---|---|
| A: | trans-3,4'-Dimethylflavanonol | 0.05 |
| | Polyoxyethylene hydrogenated castor oil | 0.8 |
| | Ginger tincture | 1.0 |
| | Isopropyl methyl phenol | 0.05 |
| | Ethanol | 55.0 |
| B: | Pyridoxine chloride | 0.1 |
| | Glycerol | 2.0 |
| | Lactic acid | suitable amount |
| | Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 26

| Hair cream | | % by weight |
|---|---|---|
| A: | trans-3,7-Dimethylflavanonol | 0.05 |
| | Vitamin B₆ | 0.05 |

Formulation Example 26

| Hair cream | % by weight |
| --- | --- |
| Liquid paraffin | 10.0 |
| Squalane | 7.0 |
| Jojoba oil | 3.0 |
| Solid paraffin | 3.0 |
| Polyoxyethylene cetyl ether | 2.0 |
| Sorbitan sesquioleate | 1.0 |
| Potassium hydroxide | 0.1 |
| B: Glycerol | 3.0 |
| Ethyl paraben | 0.1 |
| Purified water | suitable amount |

The components belonging to A are dissolved with heat. Separately, the components belonging to B are dissolved with heat. B is added to A, the resultant mixture is mixed uniformly while stirring, emulsified, and then cooled, thereby obtaining a hair cream.

Formulation Example 27

| Hair shampoo | % by weight |
| --- | --- |
| A: trans-3,4'-Dimethylflavanonol | 0.05 |
| Sulfur | 0.05 |
| Lauric acid diethanolamide | 2.0 |
| Lauric acid | 0.5 |
| Cationic polymer (Polymer JR400, Union Carbide) | 0.3 |
| Polyoxyethylene lauryl ether | 20.0 |
| B: Perfume | 0.2 |
| Citric acid | 1.5 |
| Methyl paraben | 0.1 |
| Purified water | suitable amount |

The components belonging to A are uniformly stirred and dissolved. To the resultant solution, the components belonging to B which have been uniformly dissolved in advance are added gradually, thereby obtaining a hair shampoo.

Formulation Example 28

| Hair rinse | % by weight |
| --- | --- |
| A: trans-3,7-Dimethylflavanonol | 0.05 |
| Cetanol | 3.0 |
| Propylene glycol | 2.0 |
| Liquid paraffin | 0.5 |
| Hydroxyethylcellulose (HEC Dicel SE-850) | 0.5 |
| B: Lecithin | 1.0 |
| Trimethylstearyl chloride ammonium | 1.0 |
| Methyl paraben | 0.1 |
| Citric acid | suitable amount |
| Perfume | 0.2 |
| Purified water | suitable amount |

The components belonging to A are uniformly stirred and dissolved. To the resultant solution, the components belonging to B which have been uniformly dissolved in advance are added gradually, thereby obtaining a hair rinse.

Formulation Example 29

| Hair-nourishing composition | % by weight |
| --- | --- |
| A: trans-3,4'-Dimethylflavanonol | 0.05 |
| Polyoxyethylene hydrogenated castor oil | 0.8 |
| Ethanol | 30.0 |
| B: Rosa odorata extract | 1.0 |
| Sodium dodecyl sulfate | 0.12 |
| Dodecylmethylamine oxide | 0.18 |
| Isopropyl alcohol | 15.0 |
| Benzyl alcohol | 15.0 |
| Glycerol | 2.0 |
| Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 30

| Hair tonic | % by weight |
| --- | --- |
| A: trans-3,7-Dimethylflavanonol | 0.05 |
| Polyoxyethylene hydrogenated castor oil | 0.8 |
| Ginger tincture | 1.0 |
| Isopropyl methyl phenol | 0.05 |
| Ethanol | 55.0 |
| B: Hyaluronic acid | 1.0 |
| Glycerol | 2.0 |
| Lactic acid | suitable amount |
| Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 31

| Hair cream | % by weight |
| --- | --- |
| A: trans-3,4'-Dimethylflavanonol | 0.05 |
| Liquid paraffin | 10.0 |
| Squalane | 7.0 |
| Jojoba oil | 3.0 |
| Solid paraffin | 3.0 |
| Polyoxyethylene cetyl ether | 2.0 |
| Sorbitan sesquioleate | 1.0 |
| Potassium hydroxide | 0.1 |
| B: Plant worm extract | 1.0 |
| Glycerol | 3.0 |
| Ethyl paraben | 0.1 |
| Purified water | suitable amount |

The components belonging to A are dissolved with heat. Separately, the components belonging to B are dissolved with heat. B is added to A, the resultant mixture is mixed uniformly while stirring, emulsified, and then cooled, thereby obtaining a hair cream.

Formulation Example 32

| Hair shampoo | % by weight |
| --- | --- |
| A: trans-3,7-Dimethylflavanonol | 0.05 |
| Sulfur | 0.05 |
| Lauric acid diethanolamide | 2.0 |

Formulation Example 32

| Hair shampoo | % by weight |
| --- | --- |
| Lauric acid | 0.5 |
| Cationic polymer | 0.3 |
| (Polymer JR400, Union Carbide) | |
| Polyoxyethylene lauryl ether | 20.0 |
| B: Duke extract | 1.0 |
| Perfume | 0.2 |
| Citric acid | 1.5 |
| Methyl paraben | 0.1 |
| Purified water | suitable amount |

The components belonging to A are uniformly stirred and dissolved. To the resultant solution, the components belonging to B which have been uniformly dissolved in advance are added gradually, thereby obtaining a hair shampoo.

Formulation Example 33

| Hair-nourishing composition | % by weight |
| --- | --- |
| A: trans-3,4'-Dimethylflavanonol | 0.05 |
| Polyoxyethylene hydrogenated castor oil | 0.8 |
| Ethanol | 30.0 |
| B: Cantharis extract | 1.0 |
| Sodium dodecyl sulfate | 0.12 |
| Dodecylmethylamine oxide | 0.18 |
| Isopropyl alcohol | 15.0 |
| Benzyl alcohol | 15.0 |
| Glycerol | 2.0 |
| Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 34

| Hair tonic | % by weight |
| --- | --- |
| A: trans-3,7-Dimethylflavanonol | 0.05 |
| Polyoxyethylene hydrogenated castor oil | 0.8 |
| Ginger tincture | 1.0 |
| Isopropyl methyl phenol | 0.05 |
| Ethanol | 55.0 |
| B: Camphor | 0.5 |
| Glycerol | 2.0 |
| Lactic acid | suitable amount |
| Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 35

| Hair cream | % by weight |
| --- | --- |
| A: trans-3,4'-Dimethylflavanonol | 0.05 |
| Liquid paraffin | 10.0 |
| Squalane | 7.0 |
| Jojoba oil | 3.0 |
| Solid paraffin | 3.0 |
| Polyoxyethylene cetyl ether | 2.0 |
| Sorbitan sesquioleate | 1.0 |
| Potassium hydroxide | 0.1 |
| B: Vanilyl amide nonylate | 0.05 |
| Glycerol | 3.0 |
| Ethyl paraben | 0.1 |
| Purified water | suitable amount |

The components belonging to A are dissolved with heat. Separately, the components belonging to B are dissolved with heat. B is added to A, the resultant mixture is mixed uniformly while stirring, emulsified, and then cooled, thereby obtaining a hair cream.

Formulation Example 36

| Hair-nourishing composition | % by weight |
| --- | --- |
| A: trans-3,4'-Dimethylflavanonol | 0.05 |
| Salicylic acid | 0.05 |
| Polyoxyethylene hydrogenated castor oil | 0.8 |
| Ethanol | 30.0 |
| B: Sodium dodecyl sulfate | 0.12 |
| Dodecylmethylamine oxide | 0.18 |
| Isopropyl alcohol | 15.0 |
| Benzyl alcohol | 15.0 |
| Glycerol | 2.0 |
| Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 37

| Hair-nourishing composition | % by weight |
| --- | --- |
| A: trans-3,7-Dimethylflavanonol | 0.05 |
| Ethinyl estradiol | 0.1 |
| Polyoxyethylene hydrogenated castor oil | 0.8 |
| Ethanol | 30.0 |
| B: Sodium dodecyl sulfate | 0.12 |
| Dodecylmethylamine oxide | 0.18 |
| Isopropyl alcohol | 15.0 |
| Benzyl alcohol | 15.0 |
| Glycerol | 2.0 |
| Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 38

| Hair tonic | % by weight |
| --- | --- |
| A: trans-3,4'-Dimethylflavanonol | 0.05 |
| Oxendron | 0.05 |
| Polyoxyethylene hydrogenated castor oil | 0.8 |
| Ginger tincture | 1.0 |
| Isopropyl methyl phenol | 0.05 |
| Ethanol | 55.0 |
| B: Glycerol | 2.0 |

Formulation Example 38

| Hair tonic | % by weight |
| --- | --- |
| 1-Menthol | 0.25 |
| Lactic acid | suitable amount |
| Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 39

| Hair-nourishing composition | % by weight |
| --- | --- |
| A: trans-3,4'-Dimethylflavanonol | 0.05 |
| Pentadecanocic acid glyceride | 1.0 |
| Polyoxyethylene hydrogenated castor oil | 0.8 |
| Ethanol | 30.0 |
| B: Calpronium chloride | 1.0 |
| Sodium dodecyl sulfate | 0.12 |
| Dodecylmethylamine oxide | 0.18 |
| Isopropyl alcohol | 15.0 |
| Benzyl alcohol | 15.0 |
| Glycerol | 2.0 |
| Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 40

| Hair-nourishing composition | % by weight |
| --- | --- |
| A: trans-3,7-Dimethylflavanonol | 0.05 |
| Minoxyzyl | 1.0 |
| Pentadecanocic acid glyceride | 1.0 |
| Chlormadinone acetate | 0.1 |
| Polyoxyethylene hydrogenated castor oil | 0.8 |
| Ethanol | 30.0 |
| B: Sodium dodecyl sulfate | 0.12 |
| Dodecylmethylamine oxide | 0.18 |
| Isopropyl alcohol | 15.0 |
| Benzyl alcohol | 15.0 |
| Glycerol | 2.0 |
| Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 41

| Hair-nourishing composition | % by weight |
| --- | --- |
| A: trans-3,4'-Dimethylflavanonol | 0.05 |
| Pentadecanocic acid glyceride | 1.0 |
| Oxendron | 0.05 |
| Polyoxyethylene hydrogenated castor oil | 0.8 |
| Ethanol | 30.0 |
| B: Calpronium chloride | 1.0 |
| Glycyrrhetinoic acid | 0.1 |
| Rosa odorata extract | 1.0 |
| Sodium dodecyl sulfate | 0.12 |
| Dodecylmethylamine oxide | 0.18 |
| Isopropyl alcohol | 15.0 |
| Benzyl alcohol | 15.0 |
| Glycerol | 2.0 |
| Purified water | suitable amount |

The components belonging to A are dissolved. Separately, the components belonging to B are dissolved. B is added to A, and the resultant mixture is mixed uniformly while stirring, thereby obtaining a hair-nourishing composition.

Formulation Example 42

| Hair tonic | % by weight |
| --- | --- |
| A: trans-3,7-Dimethylflavanonol | 0.05 |
| Polyoxyethylene hydrogenated castor oil | 0.8 |
| Ginger tincture | 1.0 |
| Isopropyl methyl phenol | 0.05 |
| Ethanol | 55.0 |
| B: Swertia extract | 1.0 |
| Ginseng extract | 1.0 |
| Dipotassium glycyrrhizinate | 0.1 |
| Cantharis tincture | 1.0 |
| Glycerol | 2.0 |
| 1-Menthol | 0.25 |
| Lactic acid | suitable amount |
| Purified water | suitable amount |

The components belonging to A are dissolved. Separately, the components belonging to B are dissolved. B is added to A, and the resultant mixture is mixed uniformly while stirring, thereby obtaining a hair tonic.

Formulation Example 43

| Hair-nourishing composition | % by weight |
| --- | --- |
| A: trans-3,4'-Dimethylflavanonol | 0.05 |
| Polyoxyethylene hydrogenated castor oil | 0.8 |
| Ethanol | 30.0 |
| B: Hypericum erectum extract | 1.0 |
| Sodium dodecyl sulfate | 0.12 |
| Dodecylmethylamine oxide | 0.18 |
| Isopropyl alcohol | 15.0 |
| Benzyl alcohol | 15.0 |
| Glycerol | 2.0 |
| Purified water | suitable amount |

The components belonging to A are dissolved. Separately, the components belonging to B are dissolved. B is added to A, and the resultant mixture is mixed uniformly while stirring, thereby obtaining a hair-nourishing composition.

Industrial Applicability

The hair-nourishing and hair-growing compositions of the present invention exhibit excellent hair-nourishing and hair-growing effects as well as hair loss preventing effects. Moreover, the compositions are quite safe when used over long periods.

We claim:

1. A hair nourishing composition, comprising:

an amount sufficient to nourish hair of a flavanonol derivative represented by the following formula (1):

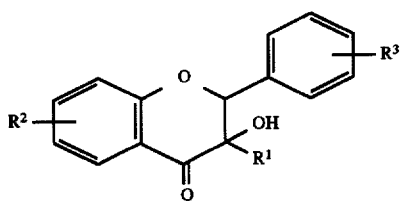

wherein

R¹ is an alkyl group,

R² is selected from the group consisting of a hydrogen atom, an alkyl group, an alkyl group having a substituent, an alkoxyl group, an alkoxyl group having a substituent, a hydroxyl group, a cyano and a halogen atom, R³ is selected from the group consisting of a hydrogen atom, an alkyl group, an alkyl group having a substituent, an alkoxyl group, an alkoxyl group having a substituent, a hydroxyl group, a cyano and a halogen atom; and at least one additional ingredient selected from the group consisting of blood flow accelerators, antibacterial agents, keratolytic agents, antiseborrheal agents, local stimulators, anti-inflammation agents, humectants, anti-androgen agents, and follicle activating agents.

2. The hair-nourishing and hair-growing composition according to claim 1, wherein, in formula (1), R¹ represents a C1–C12 alkyl group, and each of R² and R³ represents a hydrogen atom, a C1–C12 alkyl group which may be substituted by a halogen atom, a C1–C12 alkoxyl group which may be substituted by a C1–C12 alkoxyl group, a hydroxyl group, a cyano group, or a halogen atom.

3. The hair-nourishing and hair-growing composition according to claim 1, wherein the flavanonol derivative is in the form of a trans-isomer.

4. A hair nourishing composition according to claim 1, comprising a blood flow accelerator selected from the group consisting of acetylcholine, swertia extracts, ginseng extracts, gingko extracts, calpronium chloride, diphenhydramine hydrochloride, gamma-oryzanol, sacretin, chromacarim, cepharantin, nicorangyl, vitamin E, vitamin E derivatives, vitamin E nicotinate, pinacydyl, minoxyzyl, phthalides, quina extracts, Japanese iris root extracts, orange peel extracts, and citron extracts.

5. A hair nourishing composition according to claim 1, comprising an antibacterial agent selected from the group consisting of isopropylmethyl phenol, benzalconium chloride, octopirox, sensitive dye 101, sensitive dye 201, chlorohexidine, salicylic acid, zinc pyrithione, potassium sorbate, biozole, hinokitiol, and phenol.

6. A hair nourishing composition according to claim 1 comprising aspirin as a keratolytic agent.

7. A hair nourishing composition according to claim 1, comprising an antiseborrheal agent selected from the group consisting of sulfur, thioxolon, banside, polysorbates, lecithin, and cashew extracts.

8. A hair nourishing composition according to claim 1, comprising a local stimulator selected from the group consisting of camphor, 1-menthol, vanilyl amide nonylate, ginger tincture, Holland mustard extracts, cantharis tincture, zanthoxylum fruit extracts, mentha herb oil, and horseradish extracts.

9. A hair nourishing composition according to claim 1, comprising an anti-inflammation agent selected from the group consisting of azulene, guaiazulene, antihistaminic agents, hydrocortisone acetate, predonisolone, scutellaria root extracts, camomile extracts, artemisia capillaris extracts, platycodon root extracts, apricot kernel extracts, gardenia extracts, sasa veitchii extracts, gentianae extracts, symphytum officinale extracts, crataegus cuneata extracts, white birch extracts, galinsoga ciliata extracts, malva sylvestris extracts, peach kernel extracts, peach-leaf extracts, and eriobotrya japonica extracts.

10. A hair nourishing composition according to claim 1, comprising a humectant selected from the group consisting of hypericum erectum, soluble collagen, glycerol, chondroitin sulfate, tuberose polysaccharides, plant worm, trisaccharides, urea, biohyaluronic acid, hyaluronic acid, vitamin C phosphate calcium salt, sodium pyrrolidone carbonate, propylene glycol, isodonis herba extracts, hordeum vulgate extracts, orange extracts, sea-weed extracts, cucumber extracts, arctium extracts, shiitake-mushroom extracts, rehmannia root extracts, duke extracts, eriobotrya japonica extracts, grape-leaf extracts, prune extracts, luffa aegyptiaca extracts, rosa odorata extracts, minisasanishiki, lily extracts, and apple extracts.

11. A hair nourishing composition according to claim 1, comprising an anti-androgen agent selected from the group consisting of ethinyl estradiol and chlormadinone acetate.

12. A hair nourishing composition according to claim 1, comprising a follicle activating agent selected from the group consisting of N-acetyl-L-methionine, disodium adenosine triphosphate, potassium aspartate, sensitive dye 301, pentadecanoic glyceride, netakanal, ethyl pantothenate, panthenol, biotin, sodium mononitroguayacol, yeast extracts, pearl protein extracts, jujube extracts, panax rhizome, garlic components, placenta extracts, and royal jelly extracts.

13. A method of nourishing and growing hair, comprising the step of administering an effective amount of the composition of claim 1.

* * * * *